United States Patent [19]
Sanderson et al.

[11] Patent Number: 6,147,078
[45] Date of Patent: Nov. 14, 2000

[54] PYRAZINONE THROMBIN INHIBITORS

[75] Inventors: Philip E. Sanderson, Philadelphia; Matthew G. Stanton, Lansdale; Suresh K. Balani, Hatfield, all of Pa.

[73] Assignee: Merck & Co., Inc., Rahway, N.J.

[21] Appl. No.: 09/315,195

[22] Filed: May 19, 1999

Related U.S. Application Data

[60] Provisional application No. 60/085,980, May 19, 1998.
[51] Int. Cl.[7] ............... A61K 31/497; C07D 241/20; C07D 401/12
[52] U.S. Cl. ............... 514/252; 514/253; 514/255; 544/405; 544/408; 544/58.2; 544/58.6; 544/120; 544/238; 544/295; 544/357
[58] Field of Search .................. 544/405, 408; 514/252, 253, 255

[56] References Cited

U.S. PATENT DOCUMENTS

| 5,260,307 | 11/1993 | Ackermann et al. | 514/323 |
|---|---|---|---|
| 5,405,854 | 4/1995 | Ackermann et al. | 514/315 |
| 5,459,142 | 10/1995 | Tone et al. | 514/252 |
| 5,510,369 | 4/1996 | Lumma et al. | 514/422 |
| 5,744,486 | 4/1998 | Sanderson et al. | 514/318 |
| 5,866,573 | 2/1999 | Sanderson et al. | 514/235.8 |

FOREIGN PATENT DOCUMENTS

| 0 262096 A1 | 9/1987 | European Pat. Off. |
| 0 509769 A2 | 4/1992 | European Pat. Off. |
| WO 94/25051 | 11/1994 | WIPO |
| WO 96/11697 | 4/1996 | WIPO |
| WO 96/31504 | 10/1996 | WIPO |
| WO 96/32110 | 10/1996 | WIPO |
| WO 97/01338 | 1/1997 | WIPO |
| WO 97/40024 | 10/1997 | WIPO |
| WO 99/11267 | 3/1999 | WIPO |

OTHER PUBLICATIONS

Peter R. Bernstein, et al., "Nonpeptidic Inhibitors of Human Leukocyte Elastase . . . " *J. Med. Chem.*, vol. 37, 1994, pp. 3313–3326.

Sanderson, et al., "Preparation of 3–amino–2–pyrazinone–1–acetamide derivatives as thrombin inhibitors," *Chem. Abstracts* (The Amer. Chem. Soc.), vol. 128, No. 3, pp. 532–533, 22922r, Jan. 19, 1998.

*Primary Examiner*—Emily Bernhardt
*Attorney, Agent, or Firm*—Richard S. Parr; Melvin Winokur

[57] ABSTRACT

Compounds of the invention are useful in inhibiting thrombin and associated thrombotic occlusions having the following structure:

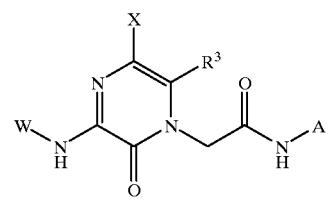

wherein

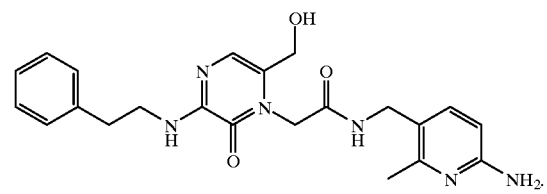

4 Claims, No Drawings

PYRAZINONE THROMBIN INHIBITORS

CROSS-REFERENCE TO RELATED APPLICATIONS

This patent application is a non-provisional paten application claiming priority to U.S. provisional application 60/085,980, filed May 19, 1998.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.*, (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., *J. Med. Chem.*, Vol. 37, pages 1259–1261 (1994) describes orally active, non-peptidic inhibitors of human leukocyte elastase which contain trifluoromethylketone and pyridinone moieties.

H. Mack et al., *J. Enzyme Inhibition*, Vol. 9, pages 73–86 (1995) describes rigid amidino-phenylalanine thrombin inhibitors which contain a pyridinone moiety as a central core structure.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention, useful as thrombin inhibitors and having therapeutic value in for example, preventing coronary artery disease, have the following structure:

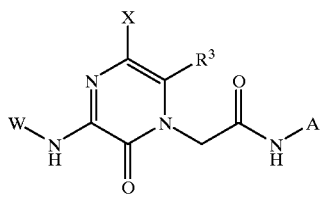

or a pharmaceutically acceptable salt thereof, wherein
A is chosen from one of the following radicals:

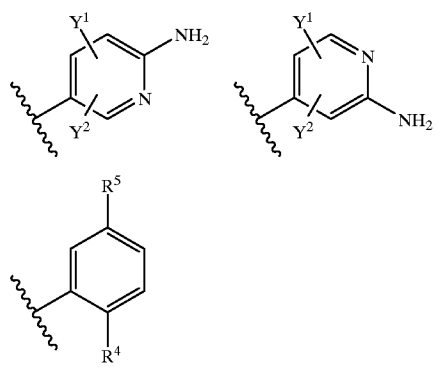

wherein $Y^1$ and $Y^2$ are independently
hydrogen;
C1–4 alkyl,
C1–4 alkoxy,
C3–7 cycloalkyl,
halogen, or
trifluoromethyl;

$R^4$ is
a) hydrogen,
b) $C_{1-4}$ alkyl,
c) $C_{1-4}$ alkoxy,
d) halogen,
e) —$OCH_2CF_3$,
f) —$OCH_2CN$,
g) —COOH,
h) —OH,
i) —$COOR^6$, where $R^6$ is $C_{1-4}$alkyl,
j) —$CONR^7R^8$, where $R^7$ and $R^8$ are independently hydrogen or $C_{1-4}$alkyl,
k) —$(CH_2)_{1-4}OH$,
l) —$CH_2NHC(O)CH_3$,
m) —$CH_2NHC(O)CF_3$,
n) —$CH_2NHSO_2CH_3$,
o) —$SO_2NH_2$,
p) —$(CH_2)_{1-4}SO_2NR^7R^8$,
q) —$(CH_2)_{1-4}SO_2R^6$,
r) a 5- to 7- membered mono- or a 9- to 10-membered bicyclic heterocyclic ring which can be saturated or unsaturated, and which contains from one to four heteroatoms selected from the group consisting of N, O and S,
s) —$ZCH_2CO_2H$, t) —$ZCH_2CO_2CH_3$,
u) —$ZCH_2R^{14}$,
v) —$ZCH_2CO_2(CH_2)_{1-3}CH_3$,
w) —$Z(CHR^9)_{1-3}C(O)NR^{10}R^{11}$,
  wherein
  $R^9$ is H or $C_{1-4}$ alkyl,
  $R^{10}$ and $R^{11}$ are independently
    i) hydrogen,
    ii) $C_{3-7}$ cycloalkyl,
    iii) aryl,
    iv) heteroaryl,
    v) heterocycloalkyl,
    vi) —$(CH_2)_{1-2}NCH_2CH_3$,
    vii) $C_{1-4}$ alkyl unsubstituted or substituted with one or more of:
      hydroxy,
      COOH,
      amino,
      aryl,
      heteroaryl, or
      heterocycloalkyl, or
  $R^{10}$ and $R^{11}$ are joined to form a four to seven membered cycloalkyl ring unsubstituted or substituted with hydroxy, amino or aryl,
  wherein Z is O, S or $CH_2$;
$R^5$ is
  hydrogen,
  halogen,
  C1–4 alkyl,
  C1–4 alkoxy,
  $CF_3$,
  CN, or
  $CO_2NH_2$; and
W is
  hydrogen,
  $R^1$,
  $R^1OCO$,
  $R^1CO$,
  $R^1(CH_2)_nNHCO$, or
  $(R^1)_2CH(CH_2)_nNHCO$,
    wherein n is 0–4;
$R^1$ is
  a) $R^2$,
  b) $R^2(CH_2)_mC(R^{12})_2$, where m is 0–3, and each $R^{12}$ can be the same or different,
  c) $(R^2)(OR^2)CH(CH_2)_p$, where p is 1–4,
  d)

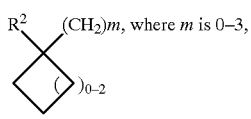

e) $R^2C(R^{12})_2(CH_2)_m$, wherein m is 0–3, and each $R^{12}$ can be the same or different, wherein $(R^{12})_2$ can also form a ring with C represented by $C_{3-7}$ cycloalkyl,
  f) $R^2CH_2C(R^{12})_2(CH_2)_q$, wherein q is 0–2, and each $R^{12}$ can be the same or different, wherein $(R^{12})_2$ can also form a ring with C represented by $C_{3-7}$ cycloalkyl,
  g) $(R^2)_2CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicylic alkyl, $C_{10-16}$ tricylic alkyl, or a 5- to 7-membered mono- or bicyclic heterocyclic ring which can be saturated or unsaturated, and which contains from one to three heteroatoms selected from the group consisting of N, O and S,
  h) $R^2O(CH_2)_p$, wherein p is 1–4,
  i) $R^2CF_2C(R^{12})_2$,
  j) $(R^2CH_2)(R^2CH_2)CH$, or
  k) $R^2(COOR^{13})(CH_2)r$, where r is 1–4;
$R^2$ is
  a) phenyl, unsubstituted or substituted with one or more of $C_{1-4}$ alkyl, $C_{1-4}$ alkoxy, halogen, hydroxy, COOH, $CONH_2$, $CH_2OH$, $CO_2R'$, where R' is $C_{1-4}$ alkyl, or $SO_2NH_2$,
  b) naphthyl,
  c) biphenyl,
  d) a 5- to 7-membered mono- or a 9- to 10-membered bicyclic heterocyclic ring or non-heterocyclic ring which can be saturated or unsaturated, wherein the heterocyclic ring contains from one to four heteroatoms selected from the group consisting of N, O and S, and wherein the heterocyclic or non-heterocyclic ring is unsubstituted or substituted with halogen or hydroxy,
  e) $C_{1-7}$ alkyl, unsubstituted or substituted with one or more of
    hydroxy,
    COOH,
    amino,
    aryl,
    $C_{3-7}$ cycloalkyl,
    $CF_3$,
    $N(CH_3)_2$,
    —$C_{1-3}$alkylaryl,
    heteroaryl, or
    heterocycloalkyl,
  f) $CF_3$
  g) $C_{3-7}$ cycloalkyl, unsubstituted or substituted with aryl,
  h) $C_{7-12}$ bicyclic alkyl, or
  i) $C_{10-16}$ tricyclic alkyl;
$R^3$ is selected from the group consisting of
  a) $YR^{15}$ wherein
    Y is O or $S(O)_n$, where n is 0, 1, or 2, and
    $R^{15}$ is H, $C_{1-4}$ alkyl or $C_{3-7}$ cycloalkyl, or
  b) $C_{1-4}$ alkyl substituted with halogen, CN, $N_3$ or $YR^{16}$, wherein
    Y is O or $S(O)_n$, where n is 0, 1, or 2, and
    $R^{16}$ is H, $C_{1-4}$ alkyl, $C_{3-7}$ cycloalkyl or aryl;
$R^{13}$ is selected from the group consisting of
  hydrogen,
  $C_{1-4}$ alkyl,
  $C_{3-7}$ cycloalkyl, or
  trifluoromethyl;
X is
  hydrogen, or
  halogen;
$R^{12}$ is
  a) hydrogen,
  b) phenyl, unsubstituted or substituted with one or more of $C_{1-4}$ alkyl, $C_{1-4}$ alkoxy, halogen, hydroxy, COOH, $CONH_2$,
  c) naphthyl,
  d) biphenyl,
  e) a 5- to 7-membered mono- or a 9- to 10-membered bicyclic heterocyclic ring which can be saturated or unsaturated, and which contains from one to four heteroatoms selected from the group consisting of N, O and S, f) C$_{1-4}$ alkyl, unsubstituted or substituted with one or more of
  hydroxy,
  COOH,
  amino,
  aryl,
  heteroaryl, or
  heterocycloalkyl,
g) CF$_3$
h) C$_{3-7}$ cycloalkyl,
i) C$_{7-12}$ bicyclic alkyl, or
j) C$_{10-16}$ tricyclic alkyl.

In a group of compounds of the invention, or a pharmaceutically acceptable salt thereof, W is
  C$_{1-7}$ alkyl, unsubstituted or substituted with one or more of
    hydroxy,
    COOH,
    amino,
    aryl,
    C$_{3-7}$ cycloalkyl,
    CF$_3$,
    N(CH$_3$)$_2$,
    —C$_{1-3}$alkylaryl,
    heteroaryl, or
    heterocycloalkyl;
X is hydrogen; and
A is

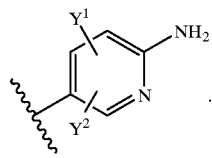

In a subgroup of this group of compounds, or a pharmaceutically acceptable salt thereof,
R$^3$ is
  —CH2OH,
  —CH2OCH3,
  —CH2SCH3,
  —CH2SPh,
  —SCH3, or
  —S(O)CH3.

One of the compounds of the invention, which is an oxidative metabolite of the compound

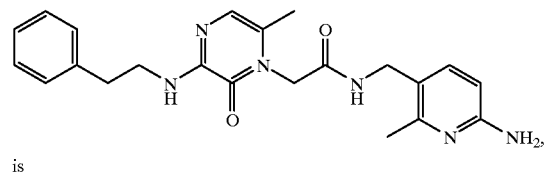

is

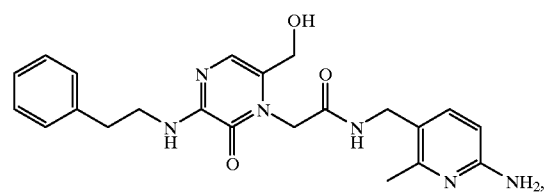

which is 3-(2-Phenethyleneamino)-6-hydroxymethyl-1-(2-methyl-6-amino-3-methylenecarboxamidomethyl)pyrazin-2-one. It is therefore within the scope of the present invention to form compounds of the invention in vivo via oxidative degradation.

Examples of compounds of the invention are listed below. Inhibitory activity of compounds of the invention is represented by "*"indicating Ki greater than or equal to 20 nM, or "**", indicating Ki less than 20 nM. Values are as determined according to the in vitro assay described later in the specification.

TABLE 1

(*.KI > 20 NM; ** KI < 20 NM)

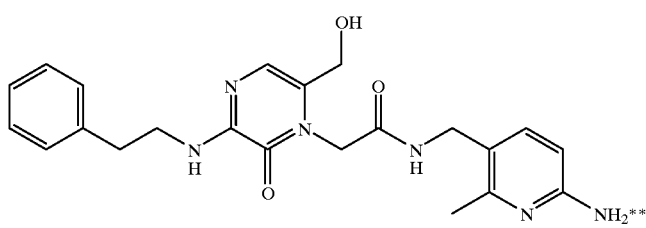

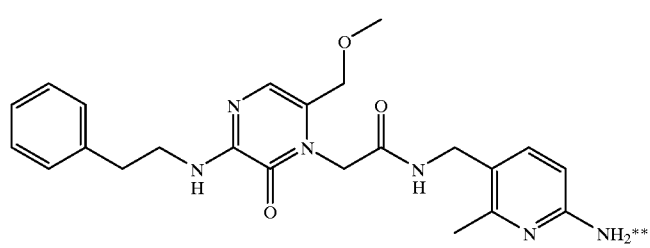

TABLE 1-continued (*.KI > 20 NM; ** KI < 20 NM)

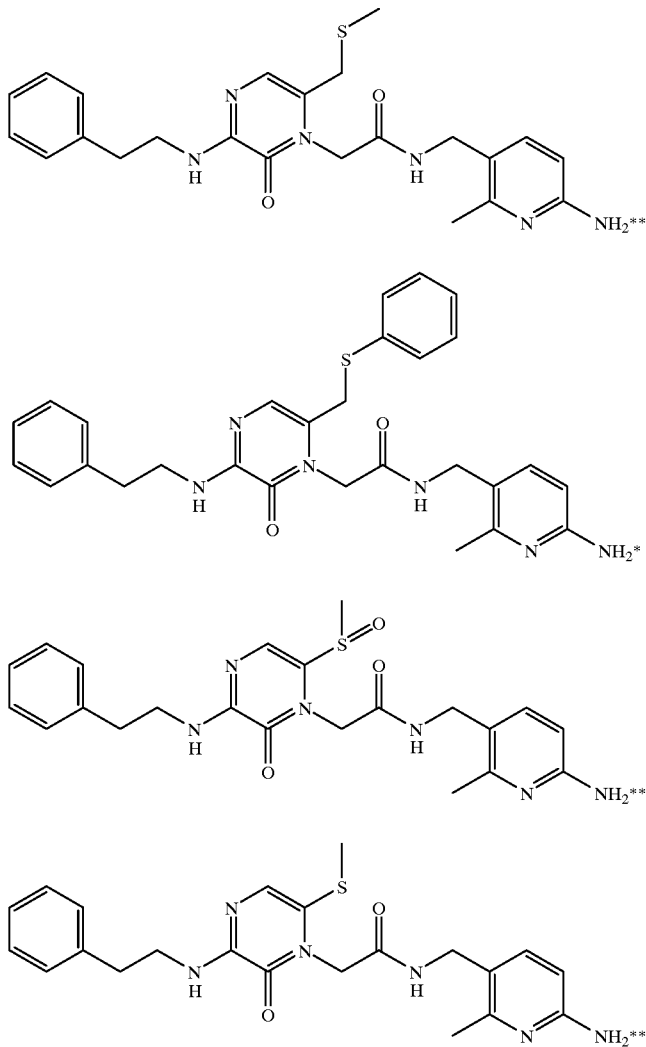

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "$C_{3-7}$cycloalkyl" is intended to include cyclopropyl, cyclobutyl, cyclopentyl, cyclohexyl and cycloheptyl, and the like.

The term "$C_{7-12}$ bicyclic alkyl" is intended to include bicyclo[2.2.1]heptyl (norbornyl), bicyclo[2.2.2]octyl, 1,1,3-trimethylbicyclo[2.2.1]heptyl (bornyl), and the like.

The term "aryl" as used herein except where noted, represents a stable 6- to 10-membered mono- or bicyclic ring system. The aryl ring can be unsubstituted or substituted with one or more of $C_{1-4}$ lower alkyl; hydroxy; alkoxy; halogen; amino. Examples of "aryl" groups include phenyl and naphthyl.

The term "heterocycle" or "heterocyclic ring", as used herein except where noted, represents a stable 5- to 7-membered mono- or bicyclic or stable 9- to 10-membered bicyclic heterocyclic ring system any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Bicyclic unsaturated ring systems include bicyclic ring systems which may be partially unsaturated or fully unsaturated. Partially unsaturated bicyclic ring systems include, for example, cyclopentenopyridinyl, benzodioxan, methylenedioxyphenyl groups. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiophenyl, oxazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl. Unsaturated heterocyclic rings may also be referred to hereinafter as "heteroaryl" rings.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Some abbreviations that may appear in this application are as follows.

| ABBREVIATIONS | |
|---|---|
| Designation | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| Activating Group | |
| HBT (HOBT or HOBt) | 1-hydroxybenzotriazole hydrate |
| Designation | Coupling Reagent |
| BOP reagent | benzotriazol-l-yloxytris-(dimethylamino)phosphonium hexafluorophosphate |
| BOP-Cl | bis(2-oxo-3-oxazolidinyl)phosphinic chloride |
| EDC | 1-ethyl-3-(3-dimethylaminopropyl) carbodiimide hydrochloride |
| | Other |
| (BOC)$_2$O (BOC$_2$O) | di-t-butyl dicarbonate |
| n-Bu$_4$N$_+$F$_-$ | tetrabutyl ammonium fluoride |
| nBuLi (n-Buli) | n-butyllithium |
| DMF | dimethylformamide |
| Et$_3$N (TEA) | triethylamine |
| EtOAc | ethyl acetate |
| TFA | trifluoroacetic acid |
| DMAP | dimethylaminopyridine |
| DME | dimethoxyethane |
| NMM | N-methylmorpholine |
| DPPA | diphenylphosphoryl azide |
| THF | tetrahydrofuran |
| DIPEA | diisopropylethylamine |
| | Amino Acid |
| Ile | Isoleucine |
| Phe | Phenylalanine |
| Pro | Proline |
| Ala | Alanine |
| Val | Valine |

IN VITRO ASSAY FOR DETERMINING PROTEINASE INHIBITION

Assays of human α-thrombin and human trypsin were performed by the methods substantially as described in *Thrombosis Research*, Issue No. 70, page 173 (1993) by S.D. Lewis et al.

The assays were carried out at 25° C. in 0.05 M TRIS buffer pH 7.4, 0.15 M NaCl, 0.1% PEG. Trypsin assays also contained 1 mM CaCl$_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human α-thrombin ($K_m$=125 μM ) and bovine trypsin ($K_m$=125 μM). p-Nitroanilide substrate concentration was determined from measurements of absorbance at 342 nm using an extinction coefficient of 8270 cm$^{-1}$M$^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration $\leq 0.1$ $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m/[S]$, $[I]/e$, and $[I]/e$ (where $[S]$, $[I]$, and e respectively represent the total concentrations, of substrate, inhibitor and enzyme), the equilibrium constant ($K_i$) for dissociation of the inhibitor from the enzyme can be obtained from the dependence of $V_o/V_i$ on $[I]$ shown in equation 1.

$$V_o/V_i = 1 + [I]/K_i \quad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. The compounds of the invention are selective compounds, as evidenced by their inhibitory activity against human trypsin (represented by Ki), which is at least 1000 nM.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethylaspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specified otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Typical tablet cores suitable for administration of thrombin inhibitors are comprised of, but not limited to, the following amounts of standard ingredients:

| EXCIPIENT | GENERAL RANGE (%) | PREFERRED RANGE (%) | MOST PREFERRED RANGE (%) |
|---|---|---|---|
| SUGGESTED RANGES OF COMPOSITION FOR EXCIPIENTS IN UNCOATED TABLET CORES | | | |
| MANNITOL | 10–90 | 25–75 | 30–60 |
| MICROCRYSTALLINE CELLULOSE | 10–90 | 25–75 | 30–60 |
| MAGNESIUM STEARATE | 0.1–5.0 | 0.1–2.5 | 0.5–1.5 |

Mannitol, microcrystalline cellulose and magnesium stearate may be substituted with alternative pharmaceutically acceptable excipients.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

THE FOLLOWING EXAMPLES ARE ILLUSTRATIVE OF THE INVENTION AS CONTEMPLATED BY THE INVENTORS AND SHOULD NOT BE CONSTRUED AS BEING LIMITS ON THE SCOPE OR SPIRIT OF THE INSTANT INVENTION.

METHOD 1 (EXEMPLIFIED BY EXAMPLE I)

STARTING 1-ETHOXYCARBONYLMETHYL-3-HYDROXY-6-METHYLPYRAZINONE IS REACTED WITH A DEHYDRATING CHLORIDE SOURCE SUCH AS PHOSPHOROUS OXYCHLORIDE IN TOLUENE TO GIVE THE 3-CHLOROPYRAZINONE IN STEP A. THIS IS BROMINATED UNDER RADICAL CONDITIONS IN STEP B USING N-BROMOSUCCINAMIDE AND AN INITIATOR SUCH AS BENZOYL PEROXIDE TO GIVE THE BROMOMETHYL DERIVATIVE. IN STEP C THE BROMINE IS DISPLACED WITH THE APPROPRIATE NUCLEOPHILE SUCH AS THIOPHENOL IN THE PRESENCE OF A BASE SUCH AS TRIETHYLAMINE. THE 3-CHLORO GROUP IS THEN DISPLACED WITH THE APPROPRIATE AMINE, IN THIS CASE PHENETHYLAMINE, TO GIVE THE 3-AMINOPYRAZINONE IN STEP D. HYDROLYSIS OF THE ESTER IN STEP E FOLLOWED BY COUPLING TO THE APPROPRIATE AMINE, IN THIS CASE 2-AMINO-5-AMINOMETHYL-6-METHYLPYRIDINE IN STEP F, GIVES THE AMIDE. THE THIOETHER MAY THEN BE OXIDISED WITH AN OXIDIZING AGENT SUCH AS M-CPBA TO GIVE THE SULFOXIDE IN STEP G. THE SULFOXIDE IS SOLVOLYSED IN AQUEOUS HCL TO GIVE THE HYDROXYMETHYL DERIVATIVE IN STEP H. BY APPROPRIATE CHOICE OF THE NUCLEOPHILIC SPECIES IN STEP H, OTHER SUBSTITUENTS MAY BE INTRODUCED IN AN ANALOGOUS FASHION.

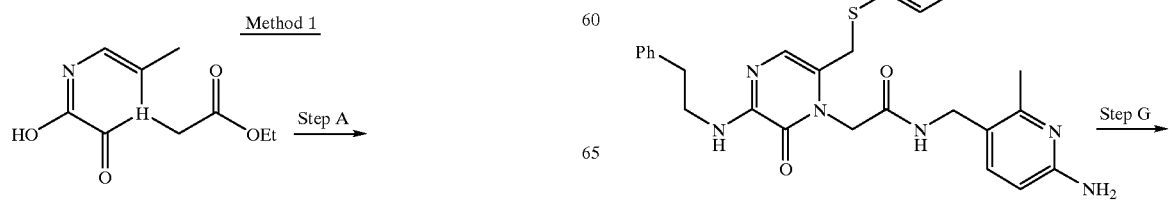

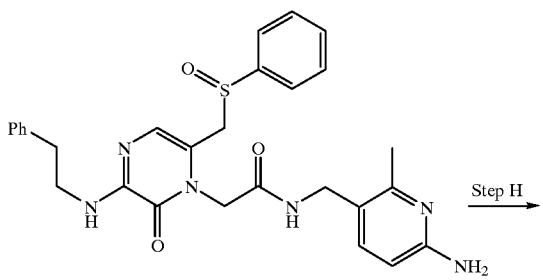

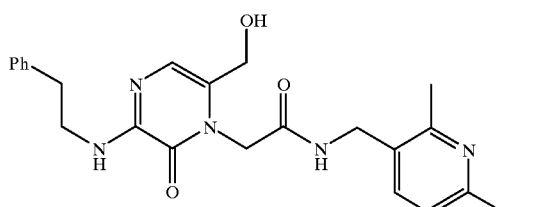

METHOD 2 (EXEMPLIFIED BY EXAMPLE IV)

STARTING 2,6-DICHLOROPYRAZINE IS REACTED WITH AMMONIA TO GIVE THE AMINOPYRAZINE IN STEP A. THE SECOND CHLORINE IS DISPLACED WITH THE APPROPRIATE NUCLEOPHILE, IN THIS CASE THIOMETHOXIDE IN STEP B TO GIVE THE THIOETHER. IN STEP C THE PYRAZINE IS BROMINATED USING AN ELECTROPHILIC SOURCE OF BROMINE SUCH AS NBS. THE AMINO GROUP AS THEN HYDROLYSED VIA THE DIAZONIUM SALT TO GIVE THE HYDROXYPYRAZINE IN STEP D. ALKYLATION WITH AN ACETATE EQUIVALENT SUCH AS T-BUTYL BROMOACETATE IN STEP E GIVES THE N-ALKYLATED PYRAZINONE. THE 3-BROMO GROUP IS THEN DISPLACED WITH THE APPROPRIATE AMINE, IN THIS CASE PHENETHYLAMINE, TO GIVE THE 3-AMINOPYRAZINONE IN STEP F. HYDROLYSIS OF THE ESTER IN STEP G FOLLOWED BY COUPLING TO THE APPROPRIATE AMINE, IN THIS CASE 2-AMINO-5-AMINOMETHYL-6-METHYLPYRIDINE IN STEP H, GIVES THE AMIDE. THE THIOETHER MAY THEN BE OXIDISED WITH AN OXIDIZING AGENT SUCH AS M-CPBA TO GIVE THE SULFOXIDE IN STEP I.

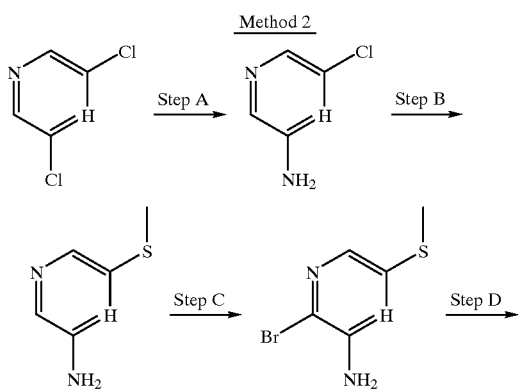

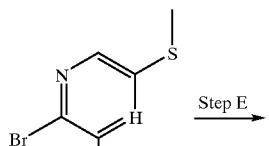

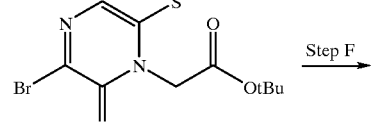

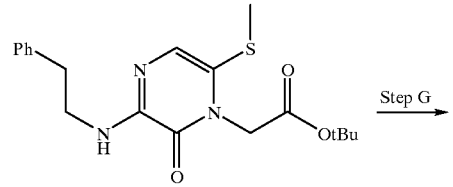

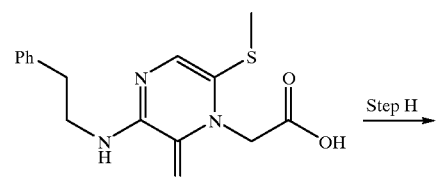

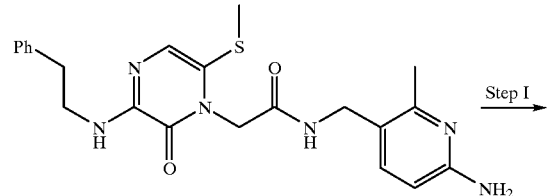

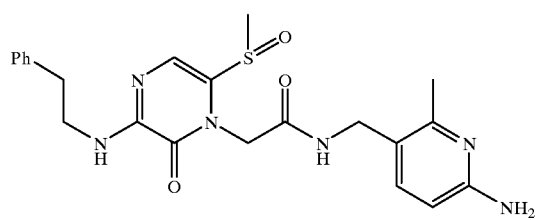

EXAMPLE I

6-HYDROXYMETHYL-3-(2-PHENETHYLAMINO)-1-(2-AMINO-6-METHYL-5-METHYLCARBOXAMIDOMETHYLPYRIDINYL)-PYRAZINONE

STEP A: 3-CHLORO-1-ETHOXYCARBONYLMETHYL-6-METHYLPYRAZINONE

PHOSPHOROUS OXYCHLORIDE (2.8 ML, 30 MMOL) WAS ADDED TO A STIRRED MIXTURE OF 1-ETHOXYCARBONYLMETHYL-3-HYDROXY-6-METHYLPYRAZINONE (5.3 G, 25 MMOL) IN DRY TOLUENE (50 ML) UNDER ARGON. THE RESULTING MIXTURE WAS HEATED TO 60° C. AFTER 64 H, THE MIXTURE WAS COOLED AND WATER AND ETHYL ACETATE WERE ADDED. THE ORGANIC LAYER WAS DRIED (NA₂SO₄) AND EVAPORATED IN VACUO. THE RESIDUE WAS PURIFIED BY FLASH COLUMN CHROMATOGRAPHY ON SILICA GEL (50% ETOAC/

HEXANES) TO GIVE THE TITLE COMPOUND AS A CRYSTALLINE SOLID:

$^1$H NMR (CDCL$_3$): Δ 1.30 (T, J=7.1 HZ, 3H), 2.25 (S, 3H), 4.27 (Q, J=7.1 HZ, 2H), 4.77 (S, 2H), 7.03 (S, 1H).

STEP B: 6-BROMOMETHYL-3-CHLORO-1-ETHOXYCARBONYLMETHYL-PYRAZINONE

N-BROMOSUCCINIMIDE (2.61 G, 14.7 MMOL) WAS ADDED TO A STIRRED SOLUTION OF 3-CHLORO-1-ETHOXYCARBONYLMETHYL-6-METHYLPYRAZINONE (3.38 G, 14.7 MMOL) IN DRY BENZENE (50 ML). BENZOYL PEROXIDE (70%, 30 MG, 0.087 MMOL) WAS ADDED AND THE SOLUTION WAS HEATED TO 75° C. AFTER 16 H THE MIXTURE WAS PARTITIONED BETWEEN METHYLENE CHLORIDE AND 5% SODIUM METABISULFITE. THE ORGANIC LAYER WAS DRIED (NA$_2$SO$_4$) AND EVAPORATED IN VACUO. THE RESIDUE WAS PURIFIED BY FLASH COLUMN CHROMATOGRAPHY ON SILICA GEL (30% ETOAC/HEXANES) TO GIVE THE TITLE COMPOUND AS A CRYSTALLINE SOLID:

$^1$H NMR (CDCL$_3$): Δ 1.32 (T, J=7.1 HZ, 3H); 4.23 (S, 2H), 4.28 (Q, J=7.1 HZ, 2H), 4.94 (S, 2H), 7.23 (S, 1H).

STEP C: 3-CHLORO-1-ETHOXYCARBONYLMETHYL-6-PHENYLTHIOMETHYL-PYRAZINONE

THIOPHENOL (1.28 ML, 12.5 MMOL) WAS ADDED DROPWISE TO A STIRRED SOLUTION OF TRIETHYLAMINE (3.0 ML, 21.5 MMOL) AND 6-BROMOMETHYL-3-CHLORO-1-ETHOXYCARBONYLMETHYLPYRAZINONE (3.86 G, 12.5 MMOL) IN METHYLENE CHLORIDE (20 ML). AFTER 15 MIN THE MIXTURE WAS PARTITIONED BETWEEN METHYLENE CHLORIDE AND WATER. THE ORGANIC LAYER WAS DRIED (NA$_2$SO$_4$) AND EVAPORATED IN VACUO TO GIVE THE TITLE COMPOUND AS A CRYSTALLINE SOLID WHICH WAS CARRIED FORWARD TO THE NEXT STEP:

$^1$H NMR (CDCL$_3$): Δ 1.32 (T, J=7.1 HZ, 3H), 3.78 (S, 2H), 4.28 (Q, J=7.1 HZ, 2H), 5.01 (S, 2H), 6.60 (S, 1H), 7.33 (S, 5H).

STEP D: 1-ETHOXYCARBONYLMETHYL-3-(2-PHENETHYLAMINO)-6-PHENYLTHIOMETHYLPYRAZINONE

PHENETHYLAMINE (3.77 ML, 30 MMOL) WAS ADDED TO A STIRRED MIXTURE 3-CHLORO-1-ETHOXYCARBONYLMETHYL-6-PHENYLTHIOMETHYLPYRAZINONE (ENTIRE PRODUCT FROM THE PREVIOUS STEP) IN TOLUENE (15 ML) UNDER ARGON AND THE RESULTING MIXTURE WAS HEATED TO REFLUX. AFTER 16 H THE REACTION WAS COOLED AND THE MIXTURE WAS PARTITIONED BETWEEN METHYLENE CHLORIDE AND WATER. THE ORGANIC LAYER WAS DRIED (NA$_2$SO$_4$) AND EVAPORATED IN VACUO. THE CRUDE PRODUCT WAS RECRYSTALLIZED FROM METHANOL TO GIVE THE TITLE COMPOUND AS A CRYSTALLINE SOLID:

$^1$H NMR (CDCL$_3$): Δ 1.30 (T, J=7.1 HZ, 3H), 2.90 (T, J=7.1 HZ, 2H), 3.62 (Q, J=7.1 HZ, 2H), 3.79 (S, 2H), 4.24 (Q, J=7.1 HZ, 2H), 4.96 (S, 2H), 6.11 (BR T, 1H), 6.49 (S, 1H), 7.19–7.39 (M, 10H).

STEP E: 1-HYDROXYCARBONYLMETHYL-3-(2-PHENETHYLAMINO)-6-PHENYLTHIOMETHYLPYRAZINONE

A SOLUTION OF LITHIUM HYDROXIDE (378 MG, 9.0 MMOL) IN WATER (10 ML) WAS ADDED TO A STIRRED SOLUTION OF 1-ETHOXYCARBONYLMETHYL-3-(2-PHENETHYLAMINO)-6-PHENYLTHIOMETHYLPYRAZINONE (3.39 G, 8.0 MMOL) IN 1:1 METHANOL/THF (20 ML). AFTER 30 MIN THE SOLUTION WAS ACIDIFIED WITH 15% KHSO$_4$ SOLUTION AND EXTRACTED WITH METHYLENE CHLORIDE. THE ORGANIC LAYER WAS DRIED (NA$_2$SO$_4$) AND EVAPORATED IN VACUO TO GIVE THE TITLE COMPOUND AS A CRYSTALLINE SOLID, MP 69–70° C.:

$^1$H NMR (CDCL$_3$): Δ 2.88 (T, J=7.1 HZ, 2H), 3.60 (BR Q, 2H), 3.78 (S, 2H), 4.98 (S, 2H), 6.26 (BR T, 1H), 6.55 (S, 1H), 7.18–7.33 (M, 10H).

STEP F: 3-(2-PHENETHYLAMINO)-6-PHENYLTHIOMETHYL-1-(2-AMINO-6-METHYL-5-METHYLCARBOXAMIDOMETHYLPYRIDINYL)-PYRAZINONE

EDC.HCL (2.3 G, 12.0 MMOL) WAS ADDED TO A STIRRED SOLUTION OF 1-HYDROXYCARBONYLMETHYL-3-(2-PHENETHYLAMINO)-6-PHENYLTHIOMETHYLPYRAZINONE (3.2 G, 8.0 MMOL), 2-AMINO-5-AMINOMETHYL-6-METHYLPYRIDINE DIHYDROCHLORIDE (1.7 G, 8.0 MMOL), HOBT.H$_2$O (2.3 G, 12.0 MMOL) AND NMM (7.7 ML, 70 MMOL) IN DMF (75 ML) AT 0° C. AFTER 16 H THE MIXTURE WAS POURED INTO WATER. THE RESULTING PRECIPITATE WAS COLLECTED BY FILTRATION, WASHING WITH WATER AND WAS DRIED TO GIVE THE TITLE COMPOUND AS A CRYSTALLINE SOLID, MP 202–203° C.:

$^1$H NMR (D$_6$DMSO): Δ 2.22 (S, 3H), 2.82 (T, J=7.1 HZ, 2H), 3.46 (BR Q, 2H), 3.99 (S, 2H), 4.12 (D, J=5.3 HZ, 2H), 4.77 (S, 2H), 6.22 (D, J=8.2 HZ, 1H), 6.60 (S, 1H), 7.11–7.35 (M, 14H), 8.45 (BR T, 1H); HRMS (FAB) C$_{28}$H$_{31}$N$_6$O$_2$S (M+1) CALCD. 515.2224. FOUND: 515.2203.

STEP G: 3-(2-PHENETHYLAMINO)-6-PHENYLSULFINYLMETHYL-1-(2-AMINO-6-METHYL-5-METHYLCARBOXAMIDOMETHYLPYRIDINYL)-PYRAZINONE

M-CPBA (55%, 2.5 G, 7.9 MMOL) WAS ADDED TO A STIRRED SOLUTION OF 3-(2-PHENETHYLAMINO)-6-PHENYLTHIOMETHYL-1-(2-AMINO-6-METHYL-5-METHYLCARBOXAMIDOMETHYLPYRIDINYL)-PYRAZINONE (4.1 G, 7.9 MMOL) IN 1:1 METHANOL/THF (300 ML). AFTER 30 MIN THE MIXTURE WAS EVAPORATED TO DRYNESS AND THE RESIDUE WAS PURIFIED BY FLASH COLUMN CHROMATOGRAPHY ON SILICA (15% METHANOL/CHLOROFORM). THE RESULTING SOLIDS WERE WASHED WITH DILUTE NAHCO$_3$ SOLUTION, WATER AND ETHANOL AND DRIED TO GIVE THE TITLE COMPOUND AS A CRYSTALLINE SOLID:

$^1$H NMR (D$_6$ DMSO): Δ 2.22 (S, 3H), 2.83 (T, J=7.4 HZ, 2H), 3.47 (BR Q, 2H), 3.95 (D, J=14.2 HZ, 1H), 4.11 (M, 2H), 4.17 (D, J=14.2 HZ, 1H), 4.77 (S, 2H), 5.77 (BR S, 2H), 6.22 (D, J=8.2 HZ, 1H), 6.35 (S, 1H), 7.18–7.31 (M, 7H), 7.53–7.60 (M, 5H), 8.49 (BR T, 1H); HRMS (FAB) C$_{28}$H$_{31}$N$_6$O$_3$S (M+1) CALCD. 531.2173. FOUND: 531.2165.

STEP H: 6-HYDROXYMETHYL-3-(2-PHENETHYLAMINO )-1-(2-AMINO-6- METHYL-5-METHYLCARBOXAMIDOMETHYLPYRIDINYL)-PYRAZINONE DIHYDROCHLORIDE

A SOLUTION OF 3-(2-PHENETHYLAMINO)-6-PHENYLSULFINYL-METHYL-1-(2-AMINO-6-METHYL-5-METHYLCARBOXAMIDOMETHYLPYRIDINYL)-PYRAZINONE (250 MG, 0.47 MMOL).IN 10:3 1M HCL/THF (13 ML) WAS STIRRED AT 50° C. FOR 1 H. THE SOLUTION WAS COOLED-AND THE VOLATILES REMOVED IN VACUO. THE RESULTING SOLUTION WAS NEUTRALISED WITH $NAHCO_3$ AND THE PRECIPITATE WAS COLLECTED BY FILTRATION, WASHING WITH WATER. THE SOLID WAS DISSOLVED IN METHANOL/4M HCL IN DIOXANE AND EVAPORATED IN VACUO. THE SOLIDS WERE TRITURATED WITH ETHYL ACETATE TO GIVE THE TITLE COMPOUND AS A CRYSTALLINE SOLID:

$^1$H NMR ($CD_3OD$): ΔΔ 2.52 (S, 3H), 3.03 (T, J=7.5 HZ, 2H), 3.72 (T, J=7.5 HZ, 2H), 4.32 (D, J=5.5 HZ, 1H), 4.37 (S, 2H), 4.87 (S, 2H), 6.70 (S, 1H), 6.83 (D, J=9.1 HZ, 1H), 7.23–7.32 (M, 5H), 7.86 (D, J=9.1 HZ, 1H), 8.80 (BR T, 1H); HRMS (FAB) $C_{22}H_{27}N_6O_3$ (M+1) CALCD. 423.2139. FOUND: 423.2130.

EXAMPLE II

6-METHOXYMETHYL-3-(2-PHENETHYLAMINO )-1-(2-AMINO-6-METHYL-5-METHYLCARBOXAMIDOMETHYLPYRIDINYL )-PYRAZINONE DIHYDROCHLORIDE

A SOLUTION OF 3-(2-PHENETHYLAMINO)-6-PHENYLSULFINYLMETHYL-1-(2-AMINO-6-METHYL-5-METHYLCARBOXAMIDOMETHYLPYRIDINYL)-PYRAZINONE (250 MG, 0.47 MMOL) IN 10:1 MEOH/ 4M HCL IN DIOXANE (11 ML) WAS STIRRED FOR 16 H. THE SOLUTION WAS EVAPORATED IN VACUO. THE SOLIDS WERE RECRYSTALLIZED (MEOH/$CHCL_3$) TO GIVE THE TITLE COMPOUND AS A CRYSTALLINE SOLID: HRMS (FAB) $C_{23}H_{29}N_6O_3$ (M+1) CALCD. 437.2296. FOUND: 437.2296.

EXAMPLE III

6-METHYLTHIOMETHYL-3-(2-PHENETHYLAMINO)-1-(2-AMINO-6-METHYL-5-METHYLCARBOXAMIDOMETHYLPYRIDINYL)-PYRAZINONE BIS-TRIFLUOROACETIC ACID SALT

THE TITLE COMPOUND WAS PREPARED AS THE FREE BASE USING THE PROCEDURES OF EXAMPLE I, STEPS C-F. THE FREE BASE WAS THEN DISSOLVED IN MEOH (1 ML) AND 4M HCL IN DIOXANE (0.5 ML) WAS ADDED. THE SOLUTION WAS EVAPORATED IN VACUO AND SOLIDS WERE WASHED WITH ETHYL ACETATE. THE RESIDUE WAS PURIFIED BY PREPARATIVE HPLC ($C_{18}$, $CH_3CN/H_2O$/0.1% TFA LINEAR GRADIENT) TO GIVE THE TITLE COMPOUND AS A GLASS: HRMS (FAB) $C_{23}H_{29}N_6O_2S$ (M+1) CALCD. 453.2067. FOUND: 453.2068.

EXAMPLE IV

6-METHYLSULFINYL-3-(2-PHENETHYLAMINO )-1-(2-AMINO-6-METHYL-5-METHYLCARBOXAMIDOMETHYLPYRIDINYL)-PYRAZINONE BIS-TRIFLUOROACETIC ACID SALT

STEP A: 6-AMINO-2-CHLOROPYRAZINE

A MIXTURE OF 2,6-DICHLOROPYRAZINE (10 G, 67.1 MMOL) AND CONCENTRATED AMMONIUM HYDROXIDE (50 ML) WERE HEATED IN A SEALED TUBE AT 140° C. FOR 16 H. THE REACTION WAS COOLED AND DILUTED WITH WATER TO GIVE A PRECIPITATE WHICH WAS COLLECTED BY FILTRATION, WASHING WITH WATER, AND DRIED TO GIVE THE TITLE COMPOUND AS A CRYSTALLINE SOLID:

$^1$H NMR ($CDCL_3$): Δ 4.78 (BR S, 2H), 7.86 (S, 1H), 7.91 (S, 1H).

STEP B: 6-AMINO-2-METHYLTHIOPYRAZINE

A MIXTURE OF 6-AMINO-2-CHLOROPYRAZINE (5.2 G, 40 MMOL) AND SODIUM THIOMETHOXIDE (3.3 G, 47 MMOL) IN DRY DMF (30 ML) WERE HEATED IN A SEALED TUBE AT 100°C. FOR 16 H. THE REACTION WAS COOLED AND PARTITIONED BETWEEN WATER AND METHYLENE CHLORIDE. THE ORGANIC LAYER WAS DRIED ($NA_2SO_4$) AND EVAPORATED IN VACUO TO GIVE THE TITLE COMPOUND AS A CRYSTALLINE SOLID:

$^1$H NMR ($CDCL_3$): Δ 2.50 (S, 3H), 4.57 (BR S, 2H), 7.62 (S, 1H), 7.81 (S, 1H).

STEP C: 3-AMINO-2-BROMO-5-METHYLTHIOPYRAZINE

NBS (3.28 G, 18.4 MMOL) WAS SLOWLY ADDED TO A STIRRED SOLUTION OF 6-AMINO-2-METHYLTHIOPYRAZINE (2.6 G, 18.4 MMOL) IN CHLOROFORM (100 ML). AFTER 1 H THE REACTION MIXTURE WAS PARTITIONED BETWEEN 10% SODIUM METABISULFITE SOLUTION AND CHLOROFORM. THE ORGANIC LAYER WAS DRIED ($NA_2SO_4$) AND EVAPORATED IN VACUO. THE CRUDE PRODUCT WAS PURIFIED BY FLASH COLUMN CHROMATOGRAPHY ON SILICA GEL (20% ETHYL ACETATE/HEXANES) TO GIVE THE TITLE COMPOUND AS A CRYSTALLINE SOLID: $^1$H NMR ($CDCL_3$): Δ 2.49 (S, 3H), 4.97 (BR S, 2H), 7.59 (S, 1H).

STEP D: 2-BROMO-3-HYDROXY-5-METHYLTHIOPYRAZINE

A SOLUTION OF SODIUM NITRITE (842 MG, 12.2 MMOL) IN WATER (100 ML) WAS ADDED TO A STIRRED SOLUTION OF 3-AMINO-2-BROMO-5-METHYLTHIOPYRAZINE (2.44 G, 11.1 MMOL) IN ACETIC ACID (100 ML) AT 0°C. THE REACTION WAS WARMED TO RT AND AFTER 16 H THE REACTION MIXTURE WAS PARTITIONED BETWEEN WATER AND METHYLENE CHLORIDE. THE ORGANIC LAYER WAS DRIED ($NA_2SO_4$) AND EVAPORATED IN VACUO. THE CRUDE PRODUCT WAS PURIFIED BY FLASH COLUMN CHROMATOGRAPHY ON SILICA GEL (40% ETHYL ACETATE/HEXANES) TO GIVE THE TITLE COMPOUND AS A CRYSTALLINE SOLID:

$^1$H NMR ($CDCL_3$): Δ 2.59 (S, 3H), 7.28 (S, 1H).

STEP E: 3-BROMO-1-T-BUTOXYCARBONYLMETHYL-6-METHYLTHIO-PYRAZINONE

SODIUM HYDRIDE (40 MG OF A 60% DISPERSION IN MINERAL OILS, 1.0 MMOL) WAS ADDED TO A

STIRRED SOLUTION OF 2-BROMO-3-HYDROXY-5-METHYLTHIOPYRAZINE (100 MG, 0.45 MMOL) IN DRY THF (10 ML) UNDER ARGON. T-BUTYL BROMOACTATE (202 MICROL, 1.5 MMOL) WAS ADDED AND THE REACTION WAS STIRRED FOR 16 H. THE VOLATILES WERE EVAPORATED IN VACUO AND THE RESIDUE WAS PARTITIONED BETWEEN WATER AND METHYLENE CHLORIDE. THE ORGANIC LAYER WAS DRIED (NA$_2$SO$_4$) AND EVAPORATED IN VACUO. THE CRUDE PRODUCT WAS PURIFIED BY FLASH COLUMN CHROMATOGRAPHY ON SILICA GEL (30% ETHYL ACETATE/HEXANES) TO GIVE THE TITLE COMPOUND AS A CRYSTALLINE SOLID:

$^1$H NMR (CDCL$_3$): Δ 1.49 (S, 9H), 2.55 (S, 3H), 4.85 (S, 2H), 7.05 (S, 1H).

STEP F: 6-METHYLTHIO-3-(2-PHENETHYLAMINO)-1-T-BUTOXYCARBONYL-METHYLPYRAZINONE

THE TITLE COMPOUND WAS PREPARED FROM PHENETHYLAMINE AND 3-BROMO-1-T-BUTOXYCARBONYLMETHYL-6-METHYLTHIOPYRAZINONE USING THE METHOD OF EXAMPLE I, STEP D, AS A CRYSTALLINE SOLID:

$^1$H NMR (CDCL$_3$): Δ 1.48 (S, 9H), 2.29 (S, 3H), 2.93 (T, J=7.1 HZ, 2H), 3.68 (Q, J=6.8 HZ, 2H), 4.91 (S, 2H), 6.26 (BR T, 1H), 7.20–7.32 (M, 6H).

STEP G: 6-METHYLTHIO-3-(2-PHENETHYLAMINO)-1-HYDROXYCARBONYL-METHYL-PYRAZINONE

A SOLUTION OF POTASSIUM HYDROXIDE (85 MG, 1.5 MMOL) IN WATER (3 ML) WAS ADDED TO A STIRRED SOLUTION OF 6-METHYLTHIO-3-(2-PHENETHYLAMINO)-1-T-BUTOXYCARBONYLMETHYLPYRAZINONE (95 MG, 0.25 MMOL) IN 1:1 MEOH/THF (5 ML). AFTER 16 H THE SOLUTION WAS ACIDIFIED WITH 10% KHSO$_4$ SOLUTION AND THE MIXTURE WAS EXTRACTED INTO ETHYL ACETATE. THE ORGANIC LAYER WAS DRIED (NA$_2$SO$_4$) AND EVAPORATED IN VACUO TO GIVE THE TITLE COMPOUND AS A CRYSTALLINE SOLID:

$^1$H NMR (CDCL$_3$): SEE LOSS OF THE T-BUTYL GROUP.

STEP H: 3-(2-PHENETHYLAMINO)-6-METHYLTHIO-1-(2-AMINO-6-METHYL-5-METHYLCARBOXAMIDOMETHYLPYRIDINYL)-PYRAZINONE DIHYDROCHLORIDE

THE TITLE COMPOUND WAS PREPARED AS THE FREE BASE FROM 1-HYDROXYCARBONYLMETHYL-3-(2-PHENETHYLAMINO)-6-METHYLTHIOPYRAZINONE AND 2-AMINO-5-AMINOMETHYL-6-METHYLPYRIDINE DIHYDROCHLORIDE USING THE PROCEDURE OF EXAMPLE I, STEP F. THE FREE BASE WAS DISSOLVED IN 1:1 MEOH/THF AND 4M HCL IN DIOXANE (1 ML) WAS ADDED. THE SOLUTION WAS EVAPORATED IN VACUO AND THE SOLIDS WERE RECRYSTALLIZED (MEOH/ETOAC) TO GIVE THE TITLE COMPOUND AS A CRYSTALLINE SOLID:

HRMS (FAB) C$_{22}$H$_{29}$N$_6$O$_2$S (M+1) CALCD. 439.1911. FOUND: 439.1911.

STEP I: 3-(2-PHENETHYLAMINO)-6-METHYLSULFINYL-1-(2-AMINO-6-METHYL-5-METHYLCARBOXAMIDOMETHYLPYRIDINYL)-PYRAZINONE BIS-TRIFLUOROACETIC ACID SALT

M-CPBA (55%, 19 MG, 0.06 MMOL) WAS ADDED TO A STIRRED SOLUTION OF 3-(2-PHENETHYLAMINO)-6-METHYLTHIO-1-(2-AMINO-6-METHYL-5-METHYLCARBOXAMIDOMETHYLPYRIDINYL)-PYRAZINONE DIHYDROCHLORIDE (30 MG, 0.06 MMOL) IN METHANOL (5 ML). AFTER 1 H THE MIXTURE WAS NEUTRALIZED WITH NAHCO$_3$ SOLUTION AND WAS DILUTED WITH WATER. THE RESULTING PRECIPITATE WAS COLLECTED BY FILTRATION, WASHING WITH WATER. THE FREE BASE WAS DISSOLVED IN MEOH (1 ML) AND 4M HCL IN DIOXANE (1 ML) WAS ADDED. THE SOLUTION WAS EVAPORATED IN VACUO AND THE SOLIDS WERE PURIFIED BY PREPARATIVE HPLC (C$_{18}$, CH$_3$CN/H$_2$O/0.1% TFA LINEAR GRADIENT) TO GIVE THE TITLE COMPOUND AS A GLASS: HRMS (FAB) C$_{22}$H$_{29}$N$_6$O$_3$S (M+1) CALCD. 455.1860. FOUND: 455.1836.

EXAMPLE V

Purification of 3-(2-Phenethyleneamino)-6-hydroxymethyl-1-(2-methyl-6-amino-3-methylenecarboxamidomethyl)pyrazin-2-one from male, bile duct-cannulated rats.

Rats were dosed intravenously with carbon 14 labeled

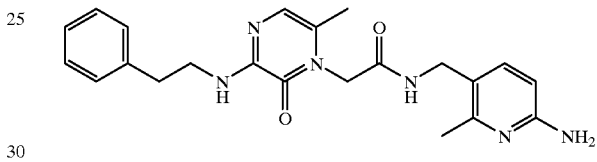

at 20 mg/kg in saline at 1 mL/kg. Bile and urine were collected periodically over 24 hours. Aliquots of these were analyzed for total radioactivity. Urine was also fractionated by HPLC using Zorbax XDB-C8 column eluted with 0.1% trifluoroacetic acid-water and acetonitrile gradient, and the fractions analyzed by mass spectrometry. A fraction eluting at about 28 minutes showed a metabolite with hydroxylation on the methylpyrazinone moiety. Exact location of the hydroxylation was determined by the application of NMR on a sample isolated by preparative HPLC, to be on the methyl group of the pyrazinone ring (i.e., 3-(2-Phenethyleneamino)-6-hydroxymethyl-1-(2-methyl-6-amino-3-methylenecarboxamidomethyl)pyrazin-2-one) as evident by the appearance of a new methylene singlet at 4.35 ppm, which showed a long-range coupling with the singlet at 6.76 ppm due to the proton at 5-position of the pyrazinone ring.

In another procedure, the urine was fractionated by HPLC. An aliquot of the fractions was assayed for total radioactivity, and the remaining volume was evaporated to dryness, under nitrogen, and bioassayed for inhibitory effect on the thrombin activity. Two of the fractions were found to contain significant inhibitory activity, one of which was 3-(2-Phenethyleneamino)-6-hydroxymethyl-1-(2-methyl-6-amino-3-methylenecarboxamidomethyl)pyrazin-2-one

EXAMPLE VI

Tablet Preparation

Tablets containing 25.0, 50.0, and 100.0 mg., respectively, of the following active compounds are prepared as illustrated below (compositions A-I). Active I is 6-Hydroxymethyl-3-(2-phenethylamino)-1-(2-amino-6-methyl-5-methylcarboxamido-methylpyridinyl)-pyrazinone; Active II is 6-Methoxymethyl-3-(2-phenethylamino)-1-(2-amino-6-methyl-5-methylcarboxamidomethyl-pyridinyl)-pyrazinone dihydrochloride; Active III 6-Methylthiomethyl-3-(2-phenethylamino)-1-(2-amino-6-methyl-5-methylcarboxamido-methylpyridinyl)-pyrazinone bis-trifluoroacetic acid salt; and Active IV is 6-Methylsulfinyl-3-(2-phenethylamino)-1-(2-amino-6-methyl-5-methylcarboxamidomethylpyridinyl)-pyrazinone bis-trifluoroacetic acid salt.

TABLE FOR DOSES CONTAINING FROM 25–100 MG OF THE ACTIVE COMPOUND

| Component | Amount-mg | | | | | | | | |
|---|---|---|---|---|---|---|---|---|---|
| | A | B | C | D | E | F | G | H | I |
| Active I | 25 | 50 | 100 | — | — | — | — | — | — |
| Active II | — | — | — | 25 | 50 | 100 | — | — | — |
| Active III | — | — | — | — | — | — | 25 | 50 | 100 |
| Microcrystalline cellulose | 37.25 | 100 | 200 | 37.25 | 100 | 200 | 37.25 | 100 | 200 |
| Modified food corn starch | 37.25 | 4.25 | 8.5 | 37.25 | 4.25 | 8.5 | 37.25 | 4.25 | 8.5 |
| Magnesium stearate | 0.5 | 0.75 | 1.5 | 0.5 | 0.75 | 1.5 | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE VII

Tablet Preparation

Exemplary compositions of 6-Methylsulfinyl-3-(2-phenethylamino)-1-(2-amino-6-methyl-5-methylcarboxamido-methylpyridinyl)-pyrazinone bis-trifluoroacetic acid-salt tablets are shown below:

| COMPONENT | 0.25 MG | 2 MG | 10 MG | 50 MG |
|---|---|---|---|---|
| ACTIVE IV | 0.500% | 1.000% | 5.000% | 14.29% |
| MANNITOL | 49.50% | 49.25% | 47.25% | 42.61% |
| MICROCRYSTALLINE CELLULOSE | 49.50% | 49.25% | 47.25% | 42.61% |
| MAGNESIUM STEARATE | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet Preparation Via Direct Compression

Active IV, mannitol and microcrystalline cellulose were sieved through mesh screens of specified size (generally 250 to 750 µm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation Via Dry Granulation

Alternatively, a dry powder blend is compacted under modest forces and remilled to afford granules of specified particle size. The granules are then mixed with magnesium stearate and tabletted as stated above.

EXAMPLE VIII

INTRAVENOUS FORMULATIONS

Intravenous aqueous formulations of 6-Methylsulfinyl-3-(2-phenethylamino)-1-(2-amino-6-methyl-5-methylcarboxamido-methylpyridinyl)-pyrazinone bis-trifluoroacetic acid salt were prepared according to general intravenous formulation procedures.

| COMPONENT | ESTIMATED RANGE |
|---|---|
| ACTIVE IV | 0.12–0.61 MG/ML |
| D-GLUCURONIC ACID* | 0.5–5 MG/ML |
| MANNITOL NF | 50–53 MG/ML |

1 N SODIUM HYDROXIDE IS USED TO ADJUST SOLUTION PH TO BETWEEN ABOUT 3.9–4.1.

Exemplary aqueous compositions A–C are as follows:

| COMPONENT | A (MG/ML) | B (MG/ML) | C (MG/ML) |
|---|---|---|---|
| ACTIVE IV | 0.61* | 0.30** | 0.15*** |
| D-GLUCURONIC ACID* | 1.94 | 1.94 | 1.94 |
| MANNITOL NF | 51.2 | 51.2 | 51.2 |

FOR EACH SOLUTION, 1 N SODIUM HYDROXIDE WAS USED TO ADJUST SOLUTION PH TO ABOUT 4.0.
*0.50 MG FREE BASE
**0.25 MG FREE BASE
***0.12 MG FREE BASE

FOR EACH SOLUTION, 1 N SODIUM HYDROXIDE WAS USED TO ADJUST SOLUTION PH TO ABOUT 4.0.

* 0.50 MG FREE BASE

** 0.25 MG FREE BASE

*** 0.12 MG FREE BASE

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound of having the formula

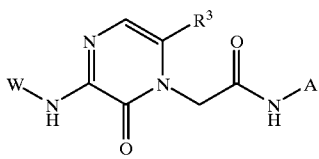

or a pharmaceutically acceptable salt thereof, wherein $R^3$ is
  —CH$_2$OH,
  —CH$_2$OCH$_3$,
  —CH$_2$SCH$_3$,
  —CH$_2$SPh,
  —SCH$_3$, or
  —S(O)CH$_3$;

W is
  $C_{1-7}$ alkyl, unsubstituted or substituted with one or more of hydroxy,
  COOH,
  amino,
  phenyl,
  naphthyl,
  $C_{3-7}$ cycloalkyl,
  CF$_3$,
  N(CH$_3$)$_2$,
  —C$_{1-3}$alkylphenyl,
  —C$_{1-3}$alkylnaphthyl, or
  heteroaryl;

A is

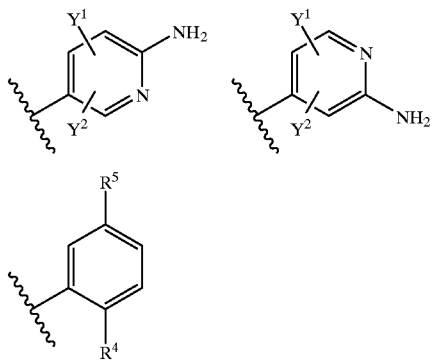

wherein $Y^1$ and $Y^2$ are independently
  hydrogaen,
  $C_{1-4}$ alkyl
  $C_{1-4}$ alkoxy,
  $C_{3-7}$ cycloalkyl,
  halogen, or
  trifluoromethyl;

$R^4$ is
  a) hydrogen,
  b) $C_{1-4}$ alkyl,
  c) $C_{1-4}$ alkoxy,
  d) halogen,
  e) —OCH$_2$CF$_3$,
  f) —OCH$_2$)CN,
  g) —COOH,
  h) —OH,
  i) —COOR$^6$, where R$^6$ is $C_{1-4}$alkyl,
  j) —CONR$^7$R$^8$, where R$^7$ and R$^8$ are independently hydrogen or $C_{1-4}$alkyl,
  k) —(CH$_2$)$_{1-4}$OH,
  l) —CH$_2$NHC(O)CH$_3$,
  m) —CH$_2$NHC(O)CF$_3$,
  n) —CH$_2$NHSO$_2$CH$_3$,
  o) —SO$_2$NH$_2$,
  p) —(CH$_2$)$_{1-4}$SO$_2$NR$^7$R$^8$,
  q) —(CH$_2$)$_{1-4}$SO$_2$R$^6$,
  r) —ZCH$_2$CO$_2$H,
  s) —ZCH$_2$CO$_2$CH$_3$,
  t) —ZCH$_2$R$^{14}$,
  u) —ZCH$_2$CO$_2$(CH$_2$)$_{1-3}$CH$_3$,
  v) —Z(CHR$^9$)$_{1-3}$C(O)NR$^{10}$R$^{11}$,
  wherein
    R$^9$ is H or $C_{1-4}$ alkyl,
    R$^{10}$ and R$^{11}$ are independently
      i) hydrogen,
      ii) $C_{3-7}$ cycloalkyl,
      iii) aryl,
      iv) heteroaryl,
      v) —(CH$_2$)$_{1-2}$NCH$_2$CH$_3$,
      vi) $C_{1-4}$ alkyl unsubstituted or substituted with one or more of:
        hydroxy,
        COOH,
        amino,
        aryl, or
        heteroaryl, or
    R$^{10}$ and R$^{11}$ are joined to form a four to seven membered cycloalkyl ring unsubstituted or substituted with hydroxy, amino or aryl,
  wherein Z is O, S or CH$_2$, and $R^5$ is
  hydrogen,
  halogen,
  $C_{1-4}$ alkyl,
  $C_{1-4}$ alkoxy,
  CF$_3$,
  CN, or
  CO$_2$NH$_2$.

2. A compound of claim 1, or a pharmaceutically acceptable salt thereof, selected from the group consisting of

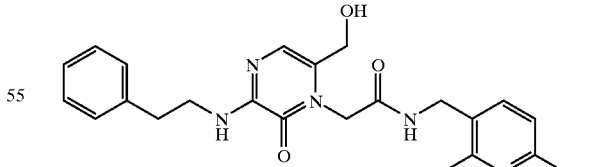

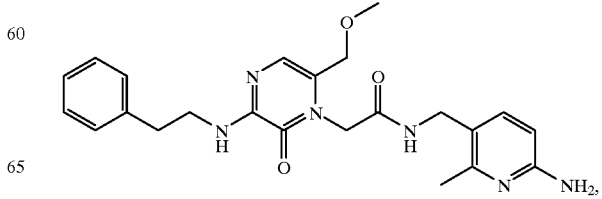

-continued
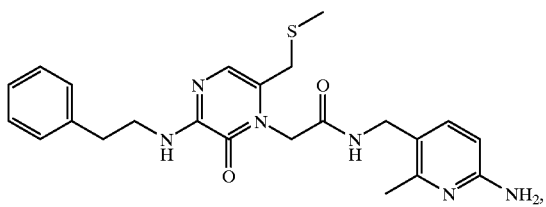
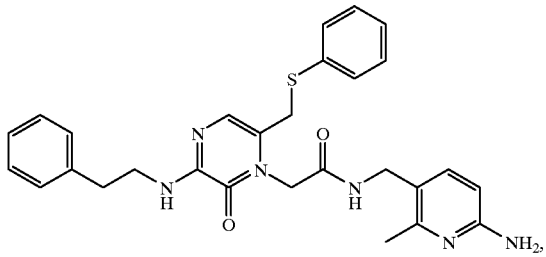
-continued
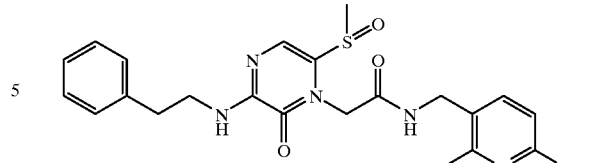
AND
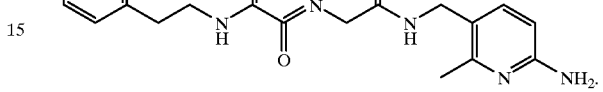
3. A pharmaceutical composition comprising a therapeutically effective amount of a compound of claim 1.
4. A method for inhibiting thrombus formation in a patient comprising treating the patient with an effective amount of a composition of claim 3.
* * * * *